United States Patent [19]

Geary et al.

[11] Patent Number: 4,991,971
[45] Date of Patent: Feb. 12, 1991

[54] FIBER OPTIC SCATTEROMETER FOR MEASURING OPTICAL SURFACE ROUGHNESS

[75] Inventors: Joseph M. Geary, Las Cruces, N. Mex.; Charles G. Hull-Allen, Jupiter, Fla.

[73] Assignee: United Technologies Corporation, Hartford, Conn.

[21] Appl. No.: 311,130

[22] Filed: Feb. 13, 1989

[51] Int. Cl.$^5$ .............................................. G01N 21/47
[52] U.S. Cl. ................................ 356/446; 250/227.29
[58] Field of Search ............... 356/446, 447, 448, 340, 356/343; 250/227, 227.29

[56] References Cited

U.S. PATENT DOCUMENTS

| | | | |
|---|---|---|---|
| 3,835,315 | 9/1974 | Gravitt, Jr. .................... | 250/227 X |
| 3,999,864 | 12/1976 | Mutter ........................... | 250/227 X |
| 4,412,746 | 11/1983 | Yokouchi ....................... | 250/227 X |
| 4,492,121 | 1/1985 | Lehto .............................. | 250/227 X |
| 4,541,719 | 9/1985 | Wyatt ................................. | 356/343 |
| 4,583,861 | 4/1986 | Yamaji et al. ....................... | 356/446 |
| 4,806,018 | 2/1989 | Falk ................................ | 50/227 X |
| 4,859,062 | 8/1989 | Thurn et al. ................... | 356/446 X |

Primary Examiner—Vincent P. McGraw
Attorney, Agent, or Firm—Perman & Green

[57] ABSTRACT

A method and apparatus for measuring scattered light reflectance. The apparatus comprises a plurality of individual light transmitting fibers having first receiving ends positioned at different angular locations about an object to be tested and second exiting ends positioned in a linear array. The apparatus can simultaneously receive different angular components of scattered light from the object being tested and convert the scattered light components into a linear array.

21 Claims, 4 Drawing Sheets

FIBER OPTIC SCATTEROMETER FOR MEASURING OPTICAL SURFACE ROUGHNESS

BACKGROUND OF THE INVENTION

1. Field of the Invention

This invention relates to measuring light reflectance and, more particularly, to a scatterometer for measuring surface scatter of light from a sample being tested and a method of doing the same.

2. Prior Art

Surface scatter of light from optical components, such as mirrors, beamsplitters, etc., is an important means of measuring the geometry of surface microstructure and thus the quality of fabrication of these optical components and the quality of the materials used in their fabrication. Generally, there are three standard methods of measuring surface scatter or the roughness of a surface; profilometry (both mechanical and optical), global type measurements (i.e: collection of all scattered light over a hemisphere in terms of the ratio of scattered light to the incident light) and bidirectional reflectance distribution function (BRDF) measurements. BRDF measures angular scatter or the amount of power/sterradian as a function of angular departure from the surface normal vector. BRDF is also usually a function of the incidence angle.

In the past, BRDF has been used because it can produce more detailed information about the interaction of light with the surface being tested than profilometry or global type measurements. Generally, a detector would be provided which would swing about a sample 180° and take sequential measurements of scattered power as a function of its angle in the plane of the incidence light beam. However, this process of moving a detector and taking sequential measurements is time consuming. In addition, the stability of the light source is critical in this sequential process to insure accurate measurements.

It is therefore an object of the present invention to provide for accurate bidirectional reflectance distribution function measurements in a fast manner.

It is a further object of the present invention to provide for parallel or simultaneous collection of data in a bidirectional reflectance distribution function measurement system.

It is a further object of the present invention to reduce the critical reliance on the stability of the light source in bidirectional reflectance distribution function measurement systems.

SUMMARY OF THE INVENTION

The foregoing problems are overcome and other advantages are provided by an instrument and method for measuring scattered light reflectance from an object being tested comprising means for simultaneously receiving different angular components of scattered light at different angles of reflectance and means for converting the different angular components into a linear array.

In accordance with one embodiment of the invention, a device for measuring scattered light reflectance from an object being tested is provided. The device comprises means for directing light at the object being tested, means for collecting reflected scattered light components from the object and a linear array detector means for reading the scattered light components and producing electrical output signals corresponding thereto. The collecting means includes a plurality of light transmitting fibers that can each receive a different angular component of the reflected scattered light at first ends and transmit the scattered light components to second ends arranged in a linear array.

In accordance with one method of the invention, a method of measuring scattered light reflectance from an object being tested comprises the steps of directing light at the object, collecting different portions of scattered light reflected from the object simultaneously at different angular locations about the object, transmitting the collected light portions from first ends of light transmitting fibers proximate the collecting locations to second ends of the fibers, the second ends being aligned in a linear array and exiting the transmitted light portions from the second ends of the fibers for reading by a linear array detector such that the detector can produce electrical output signals corresponding to the linearly exited light.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
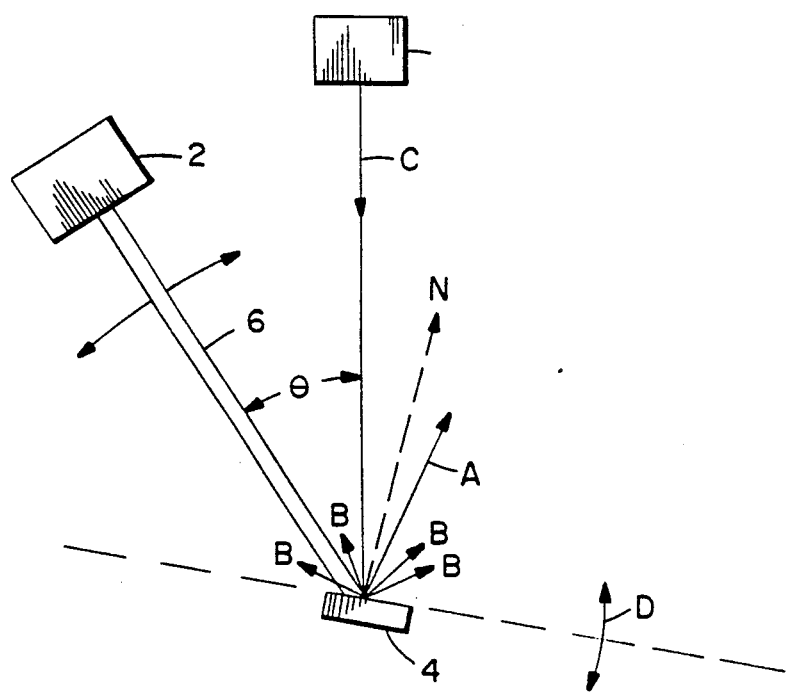
FIG. 1 is a schematic view of a bidirection reflectance distribution function measurement system known in the prior art.
Figure 1A:
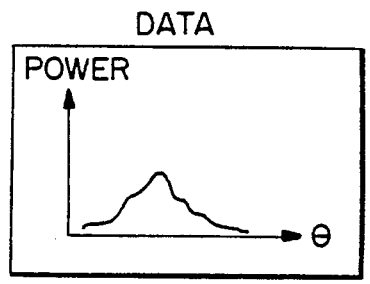
FIG. 1A is a schematic view of a bidirectional reflectance distribution function system data readout from a computer connected to the system shown in FIG. 1.

Referring to FIGS. 1 and 1A, there are shown schematic views of a bidirectional reflectance distribution function measuring system known in the prior art and its associated computer generated data readout, respectively. The device shown in FIG. 1 generally comprises a detector 2 for measuring scattered light reflectance from a sample 4 which is being tested. The detector 2 is generally mounted on a movable arm 6. A light source 8 directs a beam of light C at the sample 4 and the detector 2 is capable of swinging about the sample 4 in a 180 degree arc and measures scattered power as a function of angle $\theta$ in the plane of incidence. The specular component of the reflected light is generally indicated by arrow A and the scattered light is generally indicated by the arrows B. The sample 4 is also suitably mounted for rotation as indicated by arrow D. The detector 2 generally takes different measurements at different angles and transmits signals to a suitable microprocessor or computer such that a display as shown in FIG. IA can be produced.

Figure 2:
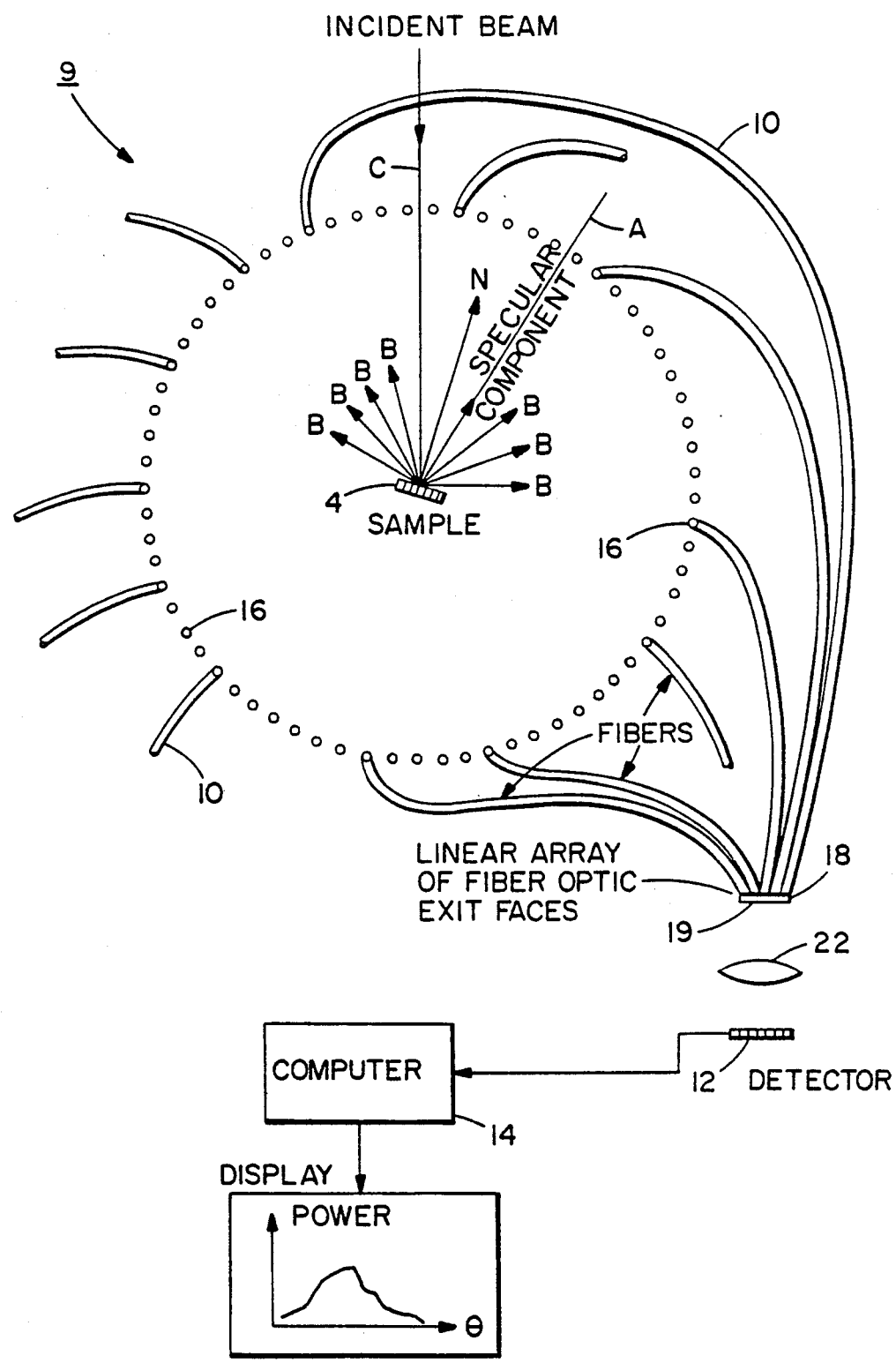
FIG. 2 is a schematic view of a fiber optic scatterometer incorporating features of the present invention.
Figure 4:
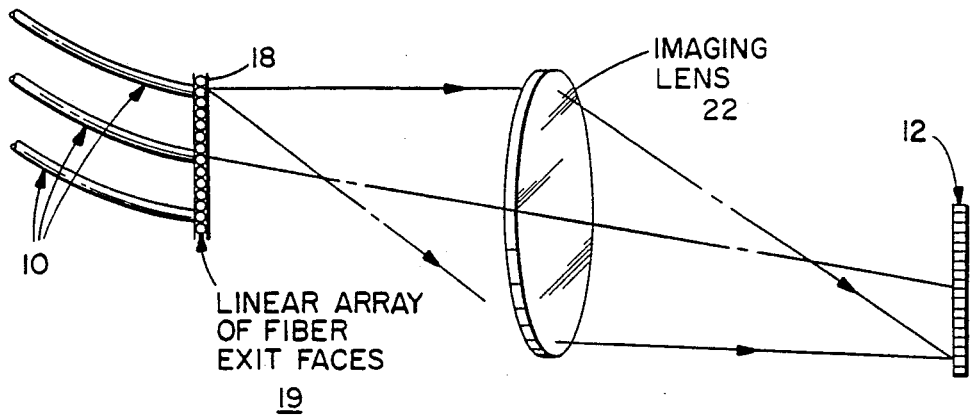
FIG. 4 is a schematic view of the linear array of fiber's exits and coupling to a linear array detector of the system shown in FIG. 2.

Referring now to FIG. 2, there is shown one embodiment of the present invention. The scatterometer 9 shown basically eliminates the cumbersome rotating detector arm 6 and sequential data taking known in the prior art device of FIG. 1. The scatterometer generally comprises a plurality of optical fibers or fiber bundles 10, a linear array detector 12 and a microprocessor or computer 14. Each of the optical fibers 10 generally comprises a first end 16 and a second end 18. The first ends 16 of the optical fibers are arranged in a circular array as shown. The second ends 18 of the optical fibers are arranged in a linear array proximate the linear array detector 12. In the embodiment shown, the first ends 16 of the optical fibers are generally provided with equal spacing between adjacent first ends 16 about the circumference of the circle, the center of which is intended to receive a suitable sample 4 to be tested. In a preferred embodiment of the invention all of the optical fibers are of equal length. Because the fibers 10 are of equal length and are substantially equidistant from the sample 4, scattered light reflected off of the sample 4 at different angles can nonetheless be collected by input couplings 30 (see FIG. 3) into the fibers 10 and simultaneously exited from the second ends 18. If the fibers 10 where of different length, then the angular components of the scattered light would not exit the second ends 18 simultaneously. In addition, because there is loss of light while the light is transmitted through the fibers 10, the losses due to the use of the fibers 10 is kept the same for each of the individual angular components because of the fibers 10 having the same length. If the fibers 10 did not have the same length, then there would be inequitable losses in different angular components resulting in incorrect measurements at the detector 12. An incident beam of light C is directed at the sample 4 from a suitable light source such as a laser (not shown) such that the incident beam C of light will pass between two adjacent first ends 16 or input couplings 30. The light, after hitting the sample 4, reflects off of the sample 4 with two main components; the specular component A and multiple scattering components B. The sample 4 is suitably angled relative to the incident light beam C such that the specular component A can pass between two adjacent first ends 16 and their associated input couplings 30.

Figure 3:
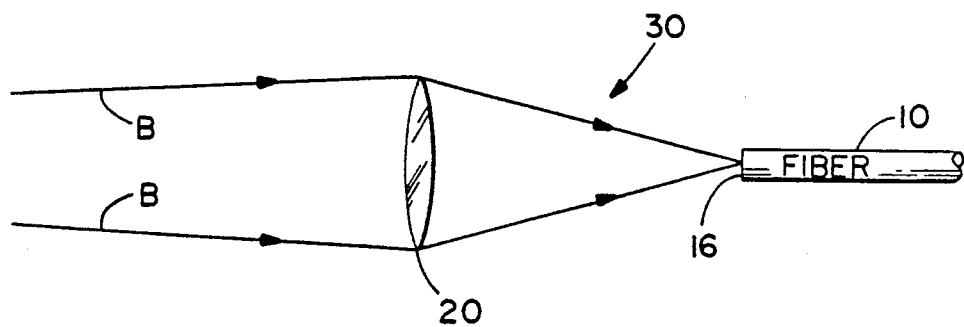
FIG. 3 is a schematic view of an input coupling to one of the fibers of the system shown in FIG. 2.

Referring also to FIG. 3, there is shown an enlarged view of an input coupling 30 to a first end 16 of an optical fiber 10. In the embodiment shown, a suitable collecting lens 20 is used to collect scattered light B and direct the collected light into the first end 16 of the fiber 10. In the embodiment in FIG. 2, a suitable lens 20 is provided for each of the first ends 16 of the fibers 10. The collecting lens 20 generally act as an input coupler such that collected scattered light can be properly focused such that it can enter the first end 16 of the fiber and travel through the fiber to its second end 18. The second ends or exit faces 18 of the fibers are arranged in a linear array 19 and monotonically with angle as per the position of the first ends or entrance faces 16. The linear array 19 of fiber exit faces 18 is then coupled to a linear array detector 12. In the embodiment shown, an imaging lens 22 is used between the exit faces 18 and the linear array detector 12 for indirect coupling. In an alternate embodiment, the exit faces 18 and the linear array detector 12 may be directly coupled to each other by butting them up against each other.

The linear array detector 12 can generally receive light components from each of the exit faces 18 and produce electrical signals which are sent to the computer 14 such that the computer can produce a display of the scattering relative to the angle $\theta$. With the embodiment shown, scattering data is generally collected in parallel or simultaneously, but read out of the detector sequentially. This procedure is generally several orders of magnitude faster than the sequential gathering of scattering data via a movable arm as shown in FIG. 1. In addition, since data is collected in parallel or simultaneously, the stability of the incident beam of light or light source is less critical in obtaining accurate data. In an alternate embodiment of the invention, a second data collecting arc or circle orthogonal to the plane of FIG. 2 and centered on the sample could be implemented thereby obtaining three-dimensional scattering information.

Figure 5:
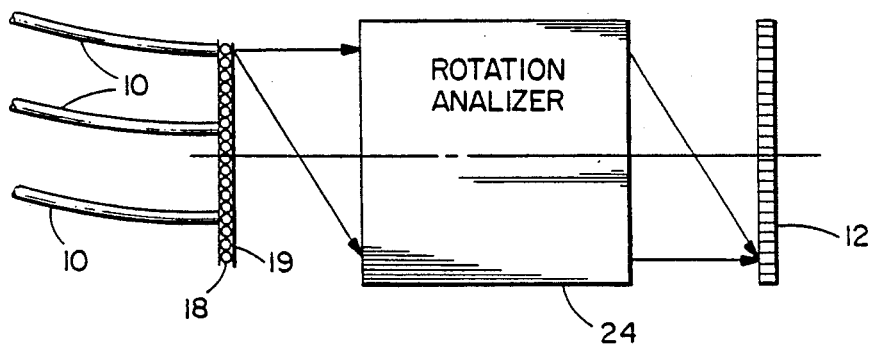
FIG. 5 is a schematic view of an alternate embodiment of the invention having polarized fiber optic fibers and a rotation analyzer.

Referring now to FIG. 5, there is shown an alternate embodiment of the invention. In the embodiment shown, the optical fibers 10 are polarization preserving fibers and a rotation analyzer 24 is provided between the linear array 19 of the second ends 18 of the fibers and the detector 12. With this embodiment, the incident beam of light C may be linearly polarized either in the plane of incidence or orthogonal to it. This embodiment can generally be provided to obtain data on polarized scattering.

Figure 6:
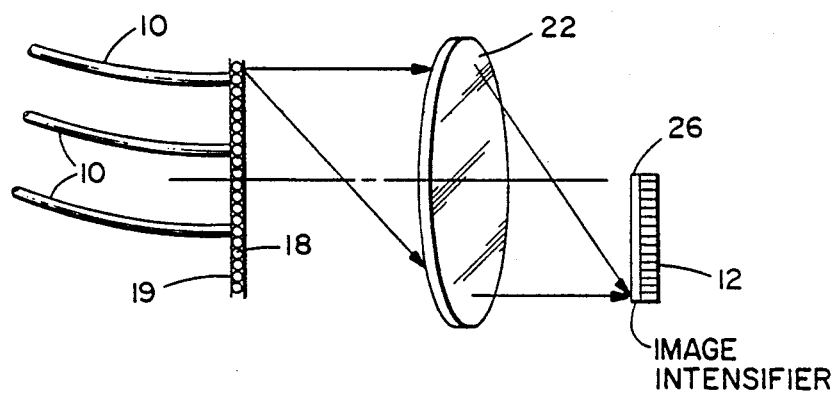
FIG. 6 is a schematic view of an alternate embodiment of the invention having an image intensifier in front of the linear array detector.

Referring to FIG. 6, there is shown another embodiment of the present invention. In the embodiment shown, a third generation image intensifier or channel plate amplifier 26 has been provided adjacent to and in front of the linear array detector 12. Because scattered light intensities from high quality optical surfaces are extremely weak, by providing the image intensifier 26 the signal levels to the computer 14 from the detector 12 can be dramatically increased. In an alternate embodiment of the invention, the image intensifier 26 can be fabricated as part of a detector package 12.

Figure 7:
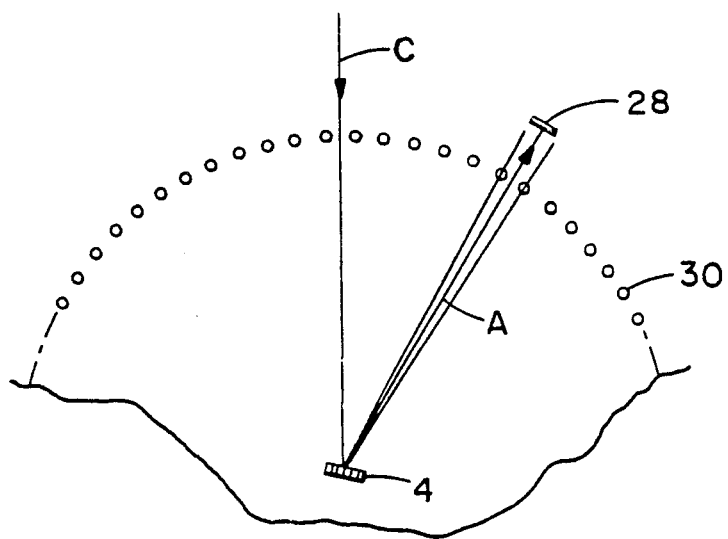
FIG. 7 is a schematic view of an alternate embodiment of the invention having an auxiliary detector.

Referring now to FIG. 7, there is shown another alternate embodiment of the invention. Generally, the specular component A of the reflected beam is adjusted to fall between a pair of input couplers 30. This avoids saturating the detection system 12. Although there is no need to have a physical surface at a location where secondary scatter from the specular component could have an effect on the primary data of interest, the embodiment shown in FIG. 7 comprises an auxiliary detector 28 to provide a reflectant measurement of the specular component. In the embodiment shown, the auxiliary detector 28 is generally provided outside the scatterometer circle such that the interception of the specular component will not interfere with the collection of the primary data of interest; scattered light. Alternatively, an auxiliary detector may be comprised of a second linear array detector for measuring small angle scattering.

As with all devices used to measure light reflectants, ambient light from operational instruments associated with tests can be compensated for. One method to compensate for ambient light is through the use of data subtraction. A data test run without the target or sample in place can be taken first and the data can later be subtracted from a data test run on the actual target or sample. This data subtraction can generally be accomplished by the use of the computer 14. In an alternate method of compensating for ambient light, the light source can be modulated and the detection system can provide for synchronous detection of the scattered light. The present invention may also be extended to the infrared wavelength ranges by providing optical fibers that can receive and transmit infrared light. In addition, the ends of the fibers may be coded with photo-luminescent material for detecting secondary radiation having wavelengths shorter or longer than the bandpass of the optical fibers.

It should be understood that the foregoing description is only illustrative of the invention. Various alternatives and modifications can be devised by those skilled in the art without departing from the spirit of the invention. Accordingly, the present invention is intended to embrace all such alternatives, modifications, and variances which fall within the scope of the appended claims.

What is claimed is:

1. A device for measuring scattered light reflectance for use in determining surface roughness of an optical surface of an object being tested, the device comprising:

means for directing light at the object being tested;

means for collecting a representative sampling of global reflected scattered light from the object, said collecting means including multiple light transmitting fibers having first ends formed along a light receptor arced path substantially equispaced from the object being tested, said fibers having equal lengths and second ends aligned in a substantially linear array such that said first ends of said fibers can each simultaneously receive a different angular component of reflected scattered light from the object being tested and independently transmit the received scattered light components to said second ends such that the transmitted scattered light components can exit said second ends simultaneously in a linear array; and linear array detector means in communication with said second ends for reading the exited scattered light components and producing individual electrical output signals corresponding thereto for measuring scattered light reflectance and determining surface roughness of the optical surface of the object.

2. A device as in claim 1 wherein each of said first ends are equally spaced from adjacent first ends and form a circular array with the object to be tested intended to be centered therein.

3. A device as in claim 1 wherein said collecting means includes input coupler means.

4. A device as in claim 3 wherein said input coupler means comprises a lens means to focus light onto said first ends.

5. A device as in claim 1 further comprising at least one additional means for collecting reflected scattered light comprising a second light receptor arced path orthogonal to the plane of said first arced path.

6. A device as in claim 1 wherein said fibers are polarization preserving fibers.

7. A device as in claim 1 wherein said means for directing light at the object comprises a light beam which is linearly polarized.

8. A device as in claim 7, further comprising a rotation analyzer means located between said second ends and said detector means such that the polarization orientation at each sampled scatter angle can be determined.

9. A device as in claim 1 wherein said detector means is directly coupled to said second ends of said fibers.

10. A device as in claim 1 further comprising means for indirectly coupling said second ends of said fibers to said detector means.

11. A device as in claim 10 wherein said coupling means comprises lens means.

12. A device as in claim 1 further comprising an image intensifier means.

13. A device as in claim 1 wherein a specular component of the reflected light from the object is adjusted to pass between a pair of fiber input couplers.

14. A device as in claim 13 further comprising means for intercepting the specular component of the reflected light from the object at a location past the receptor arced path by means of an auxiliary detector to provide a reflectance measurement.

15. A device as in claim 13 further comprising a second linear array detector means for intercepting the specular component of the reflected light from the object at a location past the receptor arced path to measure small angle scattering.

16. A device as in claim 1 further comprising means for compensating for ambient light.

17. A device as in claim 1 wherein said means for directing light at the object comprises a laser means.

18. A device as in claim 1 wherein said fibers are infrared wavelength region light transmitting fibers.

19. A device as in claim 1 wherein said first end is coated with photo-luminescent material for detecting secondary radiation.

20. A device for measuring scattered light reflectance from an optical surface of an object being tested, the device comprising:

means for simultaneously receiving a representative sample of global reflected scattered light from the optical surface of the object as different angular components, said means for receiving including first ends of a plurality of light transmitting fibers aligned in at least a semi-circular arced array equispaced from the object;

means for converting the different angular components into a linear array, said converting means comprising said light transmitting fibers having the same length and having second ends aligned in a linear array, and means for individually converting transmitted scattered light angular components into individual electrical signals corresponding thereto.

21. A method of measuring scattered light reflectance from an optical surface of an object being tested for surface roughness comprising the steps of:

directing light at the object;

collecting a representative sample along at least one plane of the scattered light simultaneously as discrete components of the total global scattered light reflected from the object at different angular locations about the object, the locations being arranged at an equispaced distance from the object in at least a semi-circular array;

transmitting the collected light components from first ends of light transmitting fibers proximate the collecting locations to second ends of the fibers, the second ends being aligned in a linear array, the fibers all having the same length;

exiting the transmitted light components from the second ends of the fibers to a linear array detector; and converting the individual light components into discrete individual electrical signals such that the detector can produce electrical output signals corresponding to the global reflected scattered light.

* * * * *